United States Patent [19]

De Clercq et al.

[11] Patent Number: 4,724,233
[45] Date of Patent: Feb. 9, 1988

[54] THERAPEUTICAL APPLICATION OF PHOSPHONYLMETHOXYALKYL ADENINES

[75] Inventors: Erik De Clercq, Louvain, Belgium; Antonín Hol, Třebešovská; Ivan Rosenberg, Obráncu mín, both of Czechoslovakia

[73] Assignees: Stichting Rega VZW, Louvain, Belgium; Ceskoslovenska Akademie VED, Prague, Czechoslovakia

[21] Appl. No.: 854,087

[22] Filed: Apr. 21, 1986

[30] Foreign Application Priority Data

Apr. 25, 1985 [CS] Czechoslovakia ................. 3018/85

[51] Int. Cl.⁴ .......................................... A61K 31/675
[52] U.S. Cl. ..................................................... 514/81
[58] Field of Search .......................................... 514/81

[56] References Cited

U.S. PATENT DOCUMENTS 4,230,708 10/1980 De Clercq et al. ................. 514/261
4,605,658 8/1986 Holy et al. ............................ 514/261

FOREIGN PATENT DOCUMENTS 2134907 8/1984 United Kingdom .

OTHER PUBLICATIONS

Chemical Abstracts, 101: 211655j, (1984).
Chemical Abstracts, 103: 6667q, (1985).
De Clercq et al., *Science*, 200, pp. 563–565, (1978).
De Clercq et al., *Antiviral Research*, 4, 119–133, (1984).
Holy et al., *Coll. CSSR Chem. Commun.*, 47, pp. 1392–1407, (1982).
De Clercq et al., *J. of Med. Chem.*, 28, pp. 282–287, (1985).

Primary Examiner—Jerome D. Goldberg
Attorney, Agent, or Firm—Birch, Stewart, Kolasch & Birch

[57] ABSTRACT

The (S) and (RS) forms of certain phosphonylmethoxyalkyl adenines and their salts have an antiviral effect against several DNA viruses and can be used for the treatment of virus diseases in human and veterinary medicine.

12 Claims, No Drawings

THERAPEUTICAL APPLICATION OF PHOSPHONYLMETHOXYALKYL ADENINES

This invention relates to a novel therapeutical agent for virus diseases and to its preparation and use.

It is known that certain substituted alkyl derivatives of adenine exhibit a marked antiviral activity. Such adenine derivatives are: 9-(S)-(2,3-dihydroxypropyl)adenine as disclosed in U.S. Pat. No. 4,230,708, D-eritadenine as disclosed by Holy et al. in Coll. Czech. Chem. Comm., 47, 1392-1407 (1982) and 3-(adenin-9-yl)-2-hydroxypropanoic acid esters as disclosed in U.S. Pat. No. 4,605,658.

Although these adenine derivatives have been indicated as broad-spectrum antiviral agents, it appears that their antiviral activity is directed predominantly against RNA-viruses such as measles, parainfluenze and vesicular stomatitis virus and further only against a single DNA-virus, viz. vaccinia virus. Their activity against the majority of DNA-viruses such as herpes simplex and herpes zoster, however, is rather minimal or totally absent.

Therefore, there is a need for antiviral adenine derivatives having their antiviral activity directed predominantly against DNA-viruses and a primary object of the invention is to provide adenine derivatives and therapeutic compositions having such activity.

In accordance with the invention, it has now been found that certain phosphonylmethoxyalkyl adenines exhibit a marked antiviral activity against several DNA-viruses such as vaccinia and herpes viruses, while being ineffective against the majority of RNA-viruses and having a low toxicity for host cells. This is surprising since antiviral activities are shown only by a limited number of adenine derivatives and since it could not be expected that the introduction of a phosphonylmethoxy group would induce such a drastic shift in antiviral activity.

The phosphonylmethoxyalkyladenines of the present invention can be represented by the following general formula (I)

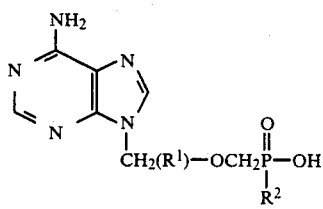

wherein $R^1$ is methylene, $-CH(OH)-CH_2-$ or

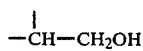

and $R^2$ *is a hydroxyl group and in some cases* $R^1$ and $R^2$ are linked with each other to form a cyclic ester group. They can be used in the form of free acids or in the form of salts such as alkalimetal, ammonium or amine salts.

Most of the compounds of formula (I), except those wherein $R^1$ is methylene, will have an asymmetric carbon atom and will exist in more than one enantiomeric form. It should be noted that, in that case, only the (S)-form of the compounds and also the racemic or (RS) form will shown sufficient antiviral activity. The best antiviral activity among the compounds of formula (I) is shown by (S)-9-(3-hydroxy-2-phosphonylmethoxypropyl)adenine.

Most of the derivatives of formula (I) are known compounds (compare GB-A-2 134 907) and therefore, the compounds as such and their chemical synthesis are not a part of the present invention.

The derivatives can be prepared in general along at least two routes, viz. (A) condensation of a 9-(hydroxyalkyl)-adenine with chloromethanephosphonylchloride followed by alkaline hydrolysis (GB-A-2 134 907) and (B) condensation of a 9-(hydroxyalkyl)-adenine with p-toluenesulphonyloxymethylenephosphoric acid diester followed by removal of the ester groups with trimethyliodosilane. Racemic mixtures can be separated into their components either before or after the preparation and if the product is a free acid, it can be converted to a salt by reaction with an alkalimetal, ammonia or with amines.

As stated before, the derivatives of formula (I) have a low toxicity for host cells. The cytotoxic effect of these derivatives on tissue culture cells is only observed at concentrations higher than 100 or 200 or 400 ug/ml, i.e. at concentrations which are substantially higher than the active virostatic concentrations (compare Table 2 below). Further, the derivatives of formula (I) are ineffective in tissue culture cells infected with the majority of RNA-viruses such as reoviruses, rhabdoviruses, paramyxoviruses, enteroviruses. Some of the derivatives are very active, however, against Moloney mouse sarcoma virus, a retrovirus which induces sarcomatous tumors in mice (compare table 3) and, therefore, these derivatives may be expected to be effective against retroviruses in general. The principal target of the compounds of formula (I) is formed by DNA-viruses like vaccinia viruses and herpes simplex virus. All such compounds inhibit the replication of several strains of herpes simplex viruses of type 1 and 2 (compare table 4). When compared to known compounds used in therapeutic compositions for the treatment of diseases caused by herpes viruses, such as Acyclovir, (E)-5-(2-bromovinyl)-2'-deoxyuridine, and 5-iodo-2'-deoxyuridine, the compounds of formula (I) are less potent; however, they lack the disadvantages of such compounds, viz. the low solubility of acyclovir, the mutagenic, teratogenic, embryotoxic and carcinogenic potential of 5-iodo-2'-deoxyuridine. An important and substantial feature of the compounds of formula (I) is their effect on those herpes virus strains which are deficient in thymidine kinase inducing activity (TK−-strains). Thymidine kinase is essential for the activity of acyclovir and (E)-5-(2-bromovinyl)-2'-deoxyuridine, which are thus inactive against TK−herpes viruses (Prusoff et al., pages 1-27 in: "Targets for the Design of Antiviral Agents", eds. De Clercq and Walker, Plenum Press, New York and London, 1984). To the contrary, the compounds of formula (I) have a distinct activity against TK−herpes viruses (compare table 4). The compounds of formula (I) can therefore be used in the therapy of diseases caused by TK−herpes virus strains and, furthermore, they may be useful in combination with acyclovir and other known compounds.

The antiviral activity of the derivatives of formula (I) is entirely novel and unexpected. It is known that phosphoric acid esters of antivirally active nucleoside analogs such as adenine arabinoside, 5-ethyl-uracil arabinoside, acyclovir, 5-iodo-2'-deoxyuridine and (E)-5-2-bromovinyl)-2'deoxyuridine, are also effective as antiviral agents. These esters merely act, however, as prodrugs and even before they have the opportunity to enter the cells, they are hydrolyzed to release the free nucleoside analogs. The compounds of formula (I) are equally polar as the above phosphoric acid esters. They can penetrate, however, as such into the cells and hence produce the desired biological effects without any hydrolysis.

Therapeutic compositions, containing compounds of formula (I) as an active ingredient for treating virus diseases in human and veterinary practice may take the form of powders, suspensions, solutions, sprays, emulsions, unguents or creams and may be used for local application (lesions of skin, mucosa, eye, etc.) for intranasal, rectal, vaginal and also for oral or parenteral (intravenous, intradermal, intramuscular, intrathecal etc.) administration. Such compositions may be prepared by combining (e.g. mixing, dissolving etc.) the active compound of formula (I) in the form of a free acid or a salt with pharmaceutically acceptable excipients of neutral character (such as aqueous or non-aqueous solvents, stabilizers, emulsifiers, detergents, additives), and further, if necessary with dyes and aromatizers. The concentration of the active ingredient in the therapeutic composition may vary widely between 0.1 percent and 100 percent, dependent from the character of the disease and the mode of administration. Further, the dose of the active ingredient to be administered may vary between 0.1 mg and 100 mg per kg of body weight.

The antiviral activity of the compounds of formula (I) is documented by the following examples which in no way limit their use. The following abbreviations are used in the examples and tables:

MCC—minimal compound concentration which brings about a microscopically detectable change in cell morphofology;

$MIC_{50}$—minimal compound concentration which will cause a 50% inhibition of the cytopathic effect of the virus;

$ID_{50}$—concentration of compound which causes a 50% decrease of incorporation of precursors labeled with tritium ($^3H$); dThd-2'-deoxythymidine; dUrd-2'-deoxyuridine; Urd-uridine; Leu-L-leucine.

Cells lines: PRK—primary tissue culture rabbit kidney cells; Vero B and Vero Flow—continuous lines of African green monkey kidney cells; HeLa—continuous line of human cervical carcinoma cells; MO—continuous murine embryonic cell line.

Designation of compounds of formula (I):

No. 1: (RS)-9-(2(3)hydroxy-3(2)-phosphonylmethoxypropyl)adenine.

No. 2: (RS)-9-(2-hydroxy-3-phosphonylmethoxypropyl)-adenine.

No. 3: (RS)-9-(2-hydroxy-3-phosphonylmethoxypropyl)-adenine.

No. 4: (S)-9-(3-hydroxy-2-phosphonylmethoxypropyl)adenine.

No. 5: 2',3'-cyclic O-phosphonylmethyl ether of (RS)-9-(2,3-dihydroxypropyl)adenine.

No. 6: 9-(2-phosphonylmethoxyethyl)adenine.

Designation of the other compounds:

(S)-DHPA, 9-(S)-(2,3-dihydroxypropyl)adenine; ACV, aclycovir; BVDU, (E)-5-(2-bromovinyl)-2'-deoxyuridine; IDU, 5-iodo-2'-deoxyuridine.

Compounds nos. 1-6 have been prepared as follows: compound no. 1 (a mixture of isomers) was prepared by reaction of (RS)-9-(2,3-dihydroxypropyl)adenine with chloromethylphosphonyl dichloride followed by an alkaline treatment. Compound no. 2 was isolated from compound no. 1 by chromatographic separation. Compounds nos. 3 and 4 were prepared by reaction of (S)-9-(2,3-dihydroxypropyl)adenine with chloromethylphosphonyl dichloride followed by an alkaline treatment and by chromatographic separation on an ion exchange resin. Compound no. 5, a mixture of isomers, was synthesized by cyclization of compound no. 1 with N,N-dicyclocarbodiimide. Compound no. 6 was prepared by reaction of 9-(2-hydroxyethyl)adenine with diethyl p-toluene sulfonyloxymethane phosphonate followed by cleavage of the ester groups.

Some physical data obtained by paper chromatography and electrophoresis are given in table 1.

TABLE 1

| Compound | $R_f$ | $E_{up}$ | k |
|---|---|---|---|
| No. 1 | 0.10 | 0.82 | 2.37 + 2.63 |
| No. 2 | 0.10 | 0.82 | 2.63 |
| No. 3 | 0.10 | 0.82 | 2.63 |
| No. 4 | 0.10 | 0.82 | 2.37 |
| No. 5 | 0.38 | 0.47 | 3.00 + 3.45 |
| No. 6 | 0.15 | 0.82 | 2.31 |

The $R_f$ values were obtained by paper chromatography in 2-propanol-conc. aqueous ammonia-water (7:1:2, vol/vol). The values of $E_{up}$ were obtained by paper electrophoresis (20 V/cm) at pH 7.5 and show the mobility related to uridine 3-phosphate. The k-values were obtained by HPLC on Separon six RPS (5/um) (4×200 mm, 0.7 ml/min.) in 5 vol.-% methanol in 0.05 mol/l triethylammonium hydrogen carbonate at pH 7.5. The detection was at 254 nm. $k=(t_r-t_o)/t_o$ when $t_r$ is the retention time and $t_o$ is the hold-up time.

EXAMPLE 1

Determination of cytotoxicity and antimetabolic activity of compounds of formula (I) in tissue cultures.

Primary rabbit kidney cell cultures were incubated in Petri dishes with solutions of compounds of formula (I) at increasing concentrations (1–400 ug/ml) in Eagle's minimum essential medium for 72 h; the morphological changes of the cells in the individual dishes were evaluated microscopically. The minimal cytotoxic concentration (MCC) shown in table 2 is the lowest concentration of the compound at which morphological changes of the cells were observed under the experimental conditions used.

For the determination of the antimetabolic effects of the compounds of formula (I), the primary rabbit kidney cell cultures in Eagle's culture medium were incubated in the presence of increasing concentrations of the compounds and a fixed amount of radiolabeled precursor. (1 uCi per dish, ($^3$H-methyl) dThd 30 Ci/mmol, ($^3$H-1',2')dUrd 27 Ci/mmol, ($^3$H-5)Urd 30 Ci/mmol, ($^3$H-4,5)Leu 47 Ci/mmol). The concentration of the labeled precursor was determined as described earlier (De Clercq et al, Biochem. Pharmac. 24, 523 (1975)). The $ID_{50}$ values of the compounds of formula (I) which cause a 50% decrease of the incorporation of the precursor compared to controls not containing the compound are listed in table 2. It is obvious from these values that none of the compounds of formula (I) shows a marked cytotoxicity and that only compounds nos. 4 and 6 specifically affect the incorporation of 2'-deoxyuridine into cells at a concentration of about 100 ug/ml.

EXAMPLE 2

Determination of antiviral effect of compounds of formula (I) in tissue cultures.

The cell cultures were infected with 100-fold the virus dose required for infection of half of the cells (100 $CCID_{50}$). 1 hour after infection, the cells were further incubated in the presence of Eagle's medium containing increasing concentrations of the compound of formula (I). Using a series of compounds assayed at different concentration the minimal compound concentration necessary to produce a 50% inhibition of the cytophatic effect of the virus ($MIC_{50}$) was determined by the method of Rosenthal and Schechmaister ("Tissue Culture", Pergamon Press, New York, p. 510, 1973). From the data presented in table 3, it is clear that compounds of formula (I) efficiently inhibit vaccinia virus, herpese simplex virus type 1 and 2 and Moloney sarcoma virus.

EXAMPLE 3

Determination of the antiviral effect of compounds of formula (I) on herpes viruses.

The experiment was carried out as described under example 2 with primary rabbit kidney (PRK) cells infected by 100 $CCID_{50}$ of various strains of herpes simples virus of type 1 and 2, and with human embryonic lung (HEL) cells infected with 20 PFU (placque-forming units) of various strains of varicella zoster virus and cytomegalovirus. The evaluation of the effect of compounds of formula (I) is given in tables 4 and 5. These data show that all the compounds were active against the cited viruses, including the TK⁻-mutants. In this respect, compound no. 4 was the most effective one.

EXAMPLE 4

Effects of compounds of formula (I) on the multiplication (yield) of herpes simplex virus type 1 and vaccinia virus.

The primary rabbit kidney cells cultures (PRK) were infected with a virus dose of $10^{4.5}$ PFU/0.5 ml (PFU being one unit of placque formation) of herpes simplex virus type 1 (strain KOS) or vaccinia virus, as described under example 2. The cells were subsequently exposed to compound (I) (at 100 ug/ml) in Eagle's culture medium.

The virus yield was determined after 1, 24, 48 and 72 h by determining the number of placques in PRK cells. The data listed on table 6 show that all compounds tested (nos. 1,2,4,5,6) decreased the yield of herpes simplex virus type 1 (KOS) and vaccinia virus by 10,000 to 100,000-fold as determined at either 1, 2 or 3 days after virus infection.

TABLE 2

Cytotoxic and antimetabolic effects of compounds of formula I on PRK cells

| Compound | MCC (μg/ml) | $ID_{50}$ (μg/ml) | | | |
|---|---|---|---|---|---|
| | | dThd | dUrd | Urd | Leu |
| No.1 | ≧100 | 250 | 230 | >400 | >400 |
| No.2 | >400 | 280 | >400 | >400 | >400 |
| No.3 | ≧200 | >400 | >400 | >400 | >400 |
| No.4 | ≧200 | 297 | 74 | >400 | >400 |
| No.5 | >400 | ≧390 | ≧360 | >400 | >400 |
| No.6 | ≧200 | 242 | 114 | >400 | >400 |
| (S)-DHPA | >400 | 350 | >400 | >400 | >400 |

TABLE 3

Effect of compounds of formula (I) on viruses in tissue culture

| Virus | Cell type | $MIC_{50}$ (μg/ml) for compound NO. | | | | | | (S)-DHPA | ACV |
|---|---|---|---|---|---|---|---|---|---|
| | | 1 | 2 | 3 | 4 | 5 | 6 | | |
| Reovirus | Vero B | >400 | >200 | >400 | >40 | >200 | >400 | 100 | — |
| Parainfluenza 3 | Vero B | >200 | >200 | >400 | >200 | >400 | >400 | 25 | — |
| Sindbis | Vero B | >400 | >400 | >400 | >400 | >400 | >400 | >400 | — |
| Coxsackie B4 | Vero B, HeLa | >400 | >400 | >400 | >400 | >400 | >200 | 130 | — |
| Polio 1 | HeLa | >400 | >400 | >400 | >400 | >400 | >400 | >400 | — |
| Measles | Vero Flow | >400 | >20 | >400 | >40 | >100 | >400 | 20 | — |
| Vesicular stomatitis | HeLa, PRK | >400 | >400 | >400 | >400 | >400 | >400 | 20 | >400 |
| Vaccinia | PRK | 0.7–3.0 | 0.3–1.0 | 15–30 | 0.3–1.5 | 0.7–3.0 | 300 | 50 | 70 |
| Herpes simplex I (KOS) | PRK | 20–30 | 2–10 | 70–150 | 1 | 30 | 15–30 | >400 | 0.2 |
| Herpes simplex 2 (G) | PRK | 7–20 | 10–15 | 30–150 | 1–3 | 30 | 7 | >400 | 0.7 |
| Moloney sarcoma | MO | >60 | 4.5 | — | 1 | >200 | 0.67 | >200 | 50 |

TABLE 4

Effect of compounds of formula I on individual strains of herpes simplex virus (HSV-1, HSV-2) in PRK cells

| Compound | $MIC_{50}$ (μg/ml) | | | | | | | |
|---|---|---|---|---|---|---|---|---|
| | HSV-1 (strain) | | | | | HSV-2 (strain) | | |
| | KOS | McIntyre | F | TK⁻ B2006 | TK⁻ C1101 | G | 196 | Lyons |
| No. 1 | 20–30 | 30 | 15–30 | 7 | 7–20 | 7–20 | 15–70 | 7–15 |
| No. 2 | 2–10 | 10–15 | 10–15 | — | 7 | 10–15 | 10–15 | 10–15 |
| No. 3 | 70–150 | 150 | 70–150 | — | 30–40 | 30–150 | 70–150 | 30–100 |
| No. 4 | 1 | 1–3 | 1–3 | 1 | 1 | 1–3 | 1–3 | 1 |
| No. 5 | 30 | 30 | 30 | — | 7 | 30 | 15 | 15 |
| No. 6 | 15–30 | 30 | — | 3 | 7 | 7 | 15 | 15 |
| ACV | 0.2 | 0.1 | 0.2 | 70 | 20 | 0.07 | 0.07 | 0.07 |
| BVDU | 0.02 | 0.02 | 0.02 | >200 | 70 | 2 | 70 | 7 |
| IDU | 0.2 | 0.2 | 0.2 | — | — | 0.2 | 2 | 0.2 |

TABLE 5

Effect of compound no. 4 on individual strains of varicella-zoster virus (VZV) and cytomegalovirus (CMV) in HEL cells

| | $MIC_{50}$ (μg/ml) | | | | | |
|---|---|---|---|---|---|---|
| | VZV (strain) | | | | CMV (strain) | |
| Compound | YS | OKa | TK⁻ YSR | TK⁻ 07-1 | Davis | AD 169 |
| No. 4 | 0.004 | 0.004 | 0.004 | 0.004 | 0.3 | 0.3 |
| ACV | 0.2 | 0.3 | 20 | 4 | 20 | 30 |
| BVDU | 0.006 | 0.007 | >400 | >400 | 300 | 200 |

TABLE 6

Effect of selected compounds of formula(I)(100 μg/ml) on multiplication of herpes simplex virus type 1 (HSV-1) (strain KOS) and vaccinia virus (VV) in PRK cell cultures

| | Titer of HSV-1 ($log_{10}$ PFU/ml) | | | | Titer of VV ($log_{10}$ PFU/ml)[a,b] | | | |
|---|---|---|---|---|---|---|---|---|
| Compound | 1 h | 24 h | 48 h | 72 h | 1 h | 24 h | 48 h | 72 h |
| No. 1 | <1.3 | 3.3 | 4.0 | 3.9 | 1.7 | 1.7 | 1.2 | 1.5 |
| No. 2 | — | <1.3 | <1.3 (<6.0) | — | 2.2 | 2.2 | 2.0(<1.3) | 1.8 |
| No. 4 | — | <1.3 | <1.3 (4.3) | — | — | — | <1.3(<1.3) | — |
| No. 5 | — | <1.3 | 2.8 (6.04) | — | 1.6 | 1.8 | <1.3(<1.3) | 1.5 |
| No. 6 | — | <1.3 | 3.34 (6.36) | — | — | — | 5.54 | — |
| Control | 1.3 | 6.7 | 6.5 | 7.0 | 2.7 | 6.1 | 6.5 | 0.3 |
| (S)-DHPA | 1.3 | 6.5 | 6.9 | 6.9 | 2.0 | 4.7 | 5.2 | 5.5 |

[a]Average of two determinations.
[b]The values in parentheses were obtained at a compound concentration of 10 μg/ml.

What we claim is:

1. A method for treating virus diseases, which comprises administering to a patient in need of said treatment an effective antiviral amount of a phosphonylmethoxyalkyladenine of the formula (I)

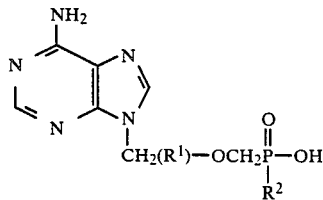

wherein $R^1$ is methylene, —CH(OH)—CH₂— or $$-\overset{|}{CH}-CH_2OH$$

and $R^2$ is a hydroxyl group, and, wherein, when $R^1$ is different from methylene, $R^1$ and $R^2$ may be linked with each other to form a cyclic ester group, said adenine derivative being in (RS) or (S) form when $R^1$ is different from methylene and further being in the form of a free acid or a salt thereof wherein the salts are selected from the group consisting of alkali metal, ammonia, and amine salts.

2. The method of claim 1, wherein said compound is (S)-9-(3-hydroxy-2-phosphonylmethoxypropyl)adenine.

3. The method of claim 1, wherein said virus disease is caused by a herpes virus.

4. A method of claim 1, wherein said virus disease is caused by pox virus.

5. The method of claim 1, wherein said virus disease is caused by a retrovirus.

6. The method of claim 1, wherein said virus disease is caused by reovirus.

7. The method of claim 1, wherein said virus disease is caused by parainfluenza virus.

8. The method of claim 1, wherein said virus disease is caused by sindbis virus.

9. The method of claim 1, wherein said virus disease is caused by polio virus.

10. The method of claim 1, wherein said virus disease is caused by vesicular stomatitis virus.

11. The method of claim 1, wherein said virus disease is caused by vaccinia.

12. The method of claim 1, wherein said virus disease is caused by moloney sarcoma virus.